United States Patent [19]

Kobzina

[11] 4,065,291
[45] Dec. 27, 1977

[54] HERBICIDAL 1-(2-HYDROXYMETHYLPYRROLIDINYL) CARBOXANILIDES

[75] Inventor: John W. Kobzina, Walnut Creek, Calif.

[73] Assignee: Chevron Research Company, San Francisco, Calif.

[21] Appl. No.: 697,498

[22] Filed: June 18, 1976

[51] Int. Cl.$^2$ ............ A01N 9/22; C07D 207/08
[52] U.S. Cl. ............................ 71/95; 260/326.4
[58] Field of Search .................. 71/95; 260/326.4

[56] References Cited

U.S. PATENT DOCUMENTS

| | | | |
|---|---|---|---|
| 3,778,247 | 12/1973 | Pyne et al. | 260/326.4 |
| 3,787,393 | 1/1974 | Aya et al. | 260/326.4 |
| 3,804,853 | 4/1974 | D'Amico et al. | 260/326.4 |
| 3,859,313 | 1/1975 | Maravetz | 260/326.4 |
| 3,933,468 | 1/1976 | Mihailovski | 71/95 |

OTHER PUBLICATIONS

D'Amico et al., German Offen. 2,039,215, Chem. Abst. vol. 74, (1971), 99859Z.

Primary Examiner—Lewis Gotts
Assistant Examiner—Catherine L. Mills
Attorney, Agent, or Firm—DixA. Newell; Raymond Owyang

[57] ABSTRACT

Herbicidal compounds of the formula

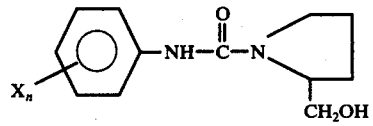

wherein X is hydrogen, fluoro, chloro, bromo, iodo, trifluoromethyl, trichloromethyl, alkyl, alkoxy or cyano and $n$ is 1, 2 or 3.

12 Claims, No Drawings

HERBICIDAL 1-(2-HYDROXYMETHYLPYRROLIDINYL) CARBOXANILIDES

DESCRIPTION OF THE PRIOR ART

German Offen. No. 2,033,908 of Pyne et al [Chem. Abs. 76 99501t(1972)] and German Offen. No. 2,039,215 of D'Amico et al [Chem. Abs. 74-99859z (1971)] disclose herbicidal pyrrolidinyl carboxanilides and thiocarboxanilides.

U.S. Pat. No. 3,639,608 of Pyne et al discloses fungicidal pyrrolidinyl carboxanilides and thiocarboxanilides.

DESCRIPTION OF THE INVENTION

The herbicidal compounds of the invention are represented by the formula

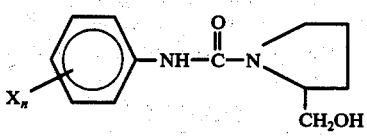

wherein X is hydrogen, fluoro, chloro, bromo, iodo, trifluoromethyl, trichloromethyl, alkyl of 1 to 4 carbon atoms, alkoxy of 1 to 4 carbon atoms or cyano and $n$ is 1, 2 or 3. When $n$ is 2 or 3, the substituents represented by X may be the same or different.

Preferred compounds of the invention are those wherein X is hydrogen, fluoro, chloro, trifluoromethyl or alkyl of 1 to 4 carbons and $n$ is 1 to 2. Most preferred compounds of the invention are those wherein X is fluoro or chloro.

The compounds of formula I can exist as the levo or dextro enantiomers or as mixtures thereof, and the present invention relates to any or all of these forms.

Representative compounds of the invention include:

1-(2-hydroxymethylpyrrolidinyl)carboxanilide,
1-(2-hydroxymethylpyrrolidinyl)-p-bromocarboxanilide
1-(2-hydroxymethylpyrrolidinyl)-o-trichloromethylcarboxanilide
1-(2-hydroxymethylpyrrolidinyl)-m-cyanocarboxanilide,
1-(2-hydroxymethylpyrrolidinyl)-p-methoxycarboxanilide,
1-(2-hydroxymethylpyrrolidinyl)-o-iodo-p-methylcarboxanilide,
1-(2-hydroxymethylpyrrolidinyl)-o-chloro-p-bromocarboxanilide.

The compounds of the invention are prepared by reacting 2-hydroxymethylpyrrolidine and a phenyl isocyanate represented by the formula

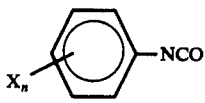

wherein X and $n$ are as previously defined. Generally, the reaction is conducted by reacting substantially equimolar amounts of the pyrrolidine and the isocyanate in an inert organic diluent at a temperature of about 0° C to 100° C. The reaction is generally complete within 1 to 24 hours. The carboxanilide product is recovered and purified by conventional procedures such as extraction, crystallization and chromatography.

EXAMPLE 1

Preparation of 1-(2-hydroxymethylpyrrolidinyl)-o-fluorocarboxanilide

A solution of 4.1 (0.03 mol) o-fluorophenyl isocyanate in 10 ml dimethoxyethane was added dropwise to a solution of 3 g (0.1 mol) 2-hydroxymethylpyrrolidine (levo-enantiomer) in 50 ml dimethoxymethane. The resulting reaction mixture was stirred for about 16 hours at 25° C. Evaporation of the dimethoxyethane under reduced pressure gave an oil which solidified on standing. The solid was stirred in ethyl ether, filtered and dried to give 4.9g product, as a white solid, m.p. 127.5°–129° C.

The compounds tabulated in Table I were prepared by a procedure similar to that described above. The structure of the compounds were vertified by quantitative elemental analysis, and by infrared spectroscopy and/or nuclear magnetic resonance analysis. Compounds Nos. 1–11 are the levo-enantiomers (prepared from levo-(2-hydroxymethylpyrrolidine)) and the compounds Nos. 12–14 are a racemic mixture of d,l-enantiomers (prepared from d,l-(2-hydroxymethylpyrroli- dine)).

EXAMPLE 2

Herbicidal Tests

The compounds of the present invention are, in general, herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broadleaved weeds. Some may be selective with respect to the type of application and/or type of weed.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atalpulgite, and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application — i.e., sheltered areas such as greenhouses, as compared to exposed areas such as fields — as well as the desired type of control. Generally for both pre- and post-emergent control, the herbicidal compounds of the invention are applied at rates of 0.2 to 60 kg/ha, and the preferred rate is in the range 0.5 to 40 kg/ha.

Pre- and post-emergent herbicidal tests on representative compounds of the invention were made using the following methods:

Pre-Emergent Test

An acetone solution of the test compound was prepared by mixing 750 mg of the compound, 220 mg of a nonionic surfactant and 25 ml of acetone. This solution was added to approximately 125 ml of water containing 156 mg of surfactant.

Seeds of the test vegetation were planted in a pot of soil and the test solution was sprayed uniformly onto the soil surface at a dose of 33 microgram/cm$^2$. The pot was watered and placed in a greenhouse. The pot was watered intermittently and was observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table II.

Post-Emergent Test

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) at a dose of 33 microgram/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table I.

EXAMPLE 3

Herbicidal Test

By a procedure similar to that of Example 2 1-(2-hydroxymethylpyrrolidinyl)-o-fluorocarboxanilide (A) and 1-(2-methylpyrrolidinyl)-o-fluorocarboxanilide (B) were tested for the control of several broadleaf weeds. The weeds tested, test concentration and results are tabulated in Table II.

TABLE II

| Compound | Lbs/Acre | Herbicidal Effectiveness | | |
|---|---|---|---|---|
| | | Lambsquarter | Mustard | Pigsweed |
| A | 2.5 | 99 | 100 | 100 |
| | 0.98 | 98 | 98 | 100 |
| | 0.39 | 96 | 95 | 100 |
| | 0.16 | 97 | 37 | 100 |
| B | 2.5 | 99 | 100 | 100 |
| | 0.98 | 100 | 89 | 100 |
| | 0.39 | 80 | 30 | 57 |
| | 0.16 | 40 | 10 | 17 |

TABLE

Structure Melting Point and Herbicidal Effectiveness of 1-(2-hydroxymethylpyrrolidinyl)carboxanilide

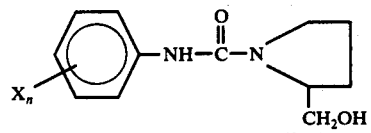

| No. | Xn | Melting Point, °C | Herbicidal Effectiveness: Pre/Post | | | | | |
|---|---|---|---|---|---|---|---|---|
| | | | O | W | C | L | M | P |
| 1 | 4-Cl | 112–115 | 0/25 | 50/50 | 25/35 | 93/100 | 40/70 | 45/100 |
| 2 | H | 108–110 | 30/0 | 40/25 | 0/20 | 85/90 | 88/90 | 88/75 |
| 3 | 2-F | 127–129 | 90/40 | 95/90 | 55/50 | 100/100 | 98/95 | 98/100 |
| 4 | 3,4-Cl$_2$ | 156–157 | 0/0 | 0/0 | 0/0 | 100/0 | 20/0 | 100/0 |
| 5 | 2-Cl | 140–141 | 10/0 | 30/20 | 30/10 | 98/70 | 90/15 | 100/80 |
| 6 | 2-CH$_2$ | 124–125 | 30/0 | 50/0 | 10/0 | 95/60 | 85/45 | 98/90 |
| 7 | 4-F | 101–106 | 45/10 | 50/40 | 60/30 | 98/100 | 98/60 | 100/95 |
| 8 | 3-F | 111–112 | 50/0 | 80/50 | 70/25 | 100/100 | 100/γ | 100/100 |
| 9 | 3-CF$_3$ | 113 | 35/0 | 25/0 | 20/0 | 98/98 | 70/65 | 98/100 |
| 10 | 3-CH$_3$ | 121–125 | 10/25 | 70/70 | 60/25 | 100/100 | 100/60 | 100/100 |
| 11 | 4-CH$_3$ | 129–130 | 20/0 | 20/0 | 20/0 | 98/93 | 20/30 | 65/95 |
| 12* | 2-F | 112–113 | 95/65 | 98/100 | 88/75 | 93/100 | 100/95 | 98/100 |
| 13* | C-CF$_3$ | 101–102 | 60/15 | 65/15 | 65/15 | 100/100 | 100/80 | 95/100 |
| 14* | 3-F | 101–102 | 93/25 | 98/100 | 95/68 | 98/95 | 100/60 | 100/100 |

*d,l-enantiomers
O = Wild Oats (Avena fatua)
W = Watergrass (Echinochloa crusgalli)
C = Crabgrass (Digitaria sanguinalis)
L = Mustard (Brassica arvensis)
M = Pigweed (Amaranthus retroflexus)
P = Lambsquarter (Chenopodium album)

What is claimed is:

1. A compound of the formula

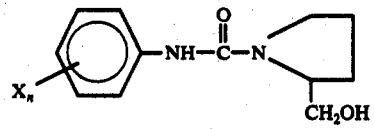

wherein X is hydrogen, fluoro, chloro, bromo, iodo, trifluoromethyl, trichloromethyl, alkyl of 1 to 4 carbon atoms, alkyl of 1 to 4 carbon atoms, alkoxy of 1 to 4 carbon atoms or cyano, and $n$ is 1, 2 or 3.

2. The compound of claim 1 wherein X is hydrogen, fluoro, chloro, trifluoromethyl, or alkyl of 1 to 4 carbon atoms and $n$ is 1 or 2.

3. The compound of claim 1 wherein X is fluoro or chloro and $n$ is 1.

4. The compound of claim 1 wherein X is o-fluoro and $n$ is 1.

5. The compound of claim 1 wherein X is 3-fluoro and $n$ is 1.

6. A method for the control of undesirable vegetation which comprises applying thereto pre-emergently or post-emergently a herbicidally effective amount of the compound defined in claim 1.

7. The method of claim 6 wherein X is hydrogen, fluoro, chloro, trifluoromethyl, or alkyl of 1 to 4 carbon atoms and $n$ is 1 or 2.

8. The method of claim 6 wherein X is o-fluoro and $n$ is 1.

9. The method of claim 6 wherein X is 3-fluoro and $n$ is 1.

10. A herbicidal composition comprising a herbicidal effective amount of the compound defined in claim 1 and a biologically inert carrier.

11. The composition of claim 10 wherein X is hydrogen, fluoro, chloro, trifluoromethyl, or alkyl of 1 to 4 carbon atoms and $n$ is 1 or 2.

12. The composition of claim 10 wherein X is o-fluoro and $n$ is 1.

* * * * *